(12) United States Patent
Horvath

(10) Patent No.: US 7,988,626 B2
(45) Date of Patent: Aug. 2, 2011

(54) LIP AND CHEEK EXPANDER

(75) Inventor: Domonkos Horvath, Jestetten (DE)

(73) Assignee: Ivoclar Vivadent AG, Schasn (LI)

( * ) Notice: Subject to any disclaimer, the term of this patent is extended or adjusted under 35 U.S.C. 154(b) by 902 days.

(21) Appl. No.: 11/954,147

(22) Filed: Dec. 11, 2007

(65) Prior Publication Data

US 2008/0153058 A1   Jun. 26, 2008

Related U.S. Application Data

(63) Continuation of application No. 10/468,934, filed as application No. PCT/EP02/14342 on Dec. 16, 2002, now abandoned.

(30) Foreign Application Priority Data

Dec. 17, 2001  (CH) ........................................ 2305/01

(51) Int. Cl.
*A61B 1/32* (2006.01)
(52) U.S. Cl. ...................................................... 600/237
(58) Field of Classification Search .................. 600/236, 600/237, 238; 433/136, 138, 140; 128/849, 128/850, 856, 859, 861
See application file for complete search history.

(56) References Cited

U.S. PATENT DOCUMENTS

| | | | |
|---|---|---|---|
| 2,589,504 | A | 3/1952 | Miller |
| 2,812,758 | A | 11/1957 | Blumneschein |
| 3,332,417 | A | 7/1967 | Blanford et al. |
| 4,984,564 | A | 1/1991 | Yuen |
| 5,366,478 | A | 11/1994 | Brinkerhoff et al. |
| 5,524,644 | A | 6/1996 | Crook |
| 5,590,643 | A | 1/1997 | Flam |
| 5,632,284 | A | 5/1997 | Graether |
| 6,017,304 | A | 1/2000 | Vierra et al. |
| 6,254,533 | B1 | 7/2001 | Fadem et al. |
| 6,254,534 | B1 | 7/2001 | Butler et al. |
| 6,450,983 | B1 | 9/2002 | Rambo |
| 2001/0037053 | A1 | 11/2001 | Bonadio et al. |

*Primary Examiner* — Eduardo C Robert
*Assistant Examiner* — David Comstock
(74) *Attorney, Agent, or Firm* — Ann M. Knab

(57) ABSTRACT

A lip and cheek expander for use when performing dental medicine, dental hygiene or dental-documenting activities has two tensioning frames (1, 2) and non-profiled film-like means (3) connecting the tensioning frames (1, 2). When the expander is fitted, the inner tensioning frame (1) inside the oral cavity and the outer tensioning frame outside lies against the lips and cheeks. The film-like means (3) are connected at one end to the inner tensioning frame (1) and at the other end to the outer tensioning frame (2). The film-like means (3) oppose forces (5) to the closure and contraction forces of the lips and cheek muscles and conduct them away onto the tensioning frames (1, 2). The mouth opening is thereby kept open and the lips and cheeks held back from the rows of teeth. A closing of the mouth is also possible when the lip and cheek expander is fitted.

26 Claims, 5 Drawing Sheets

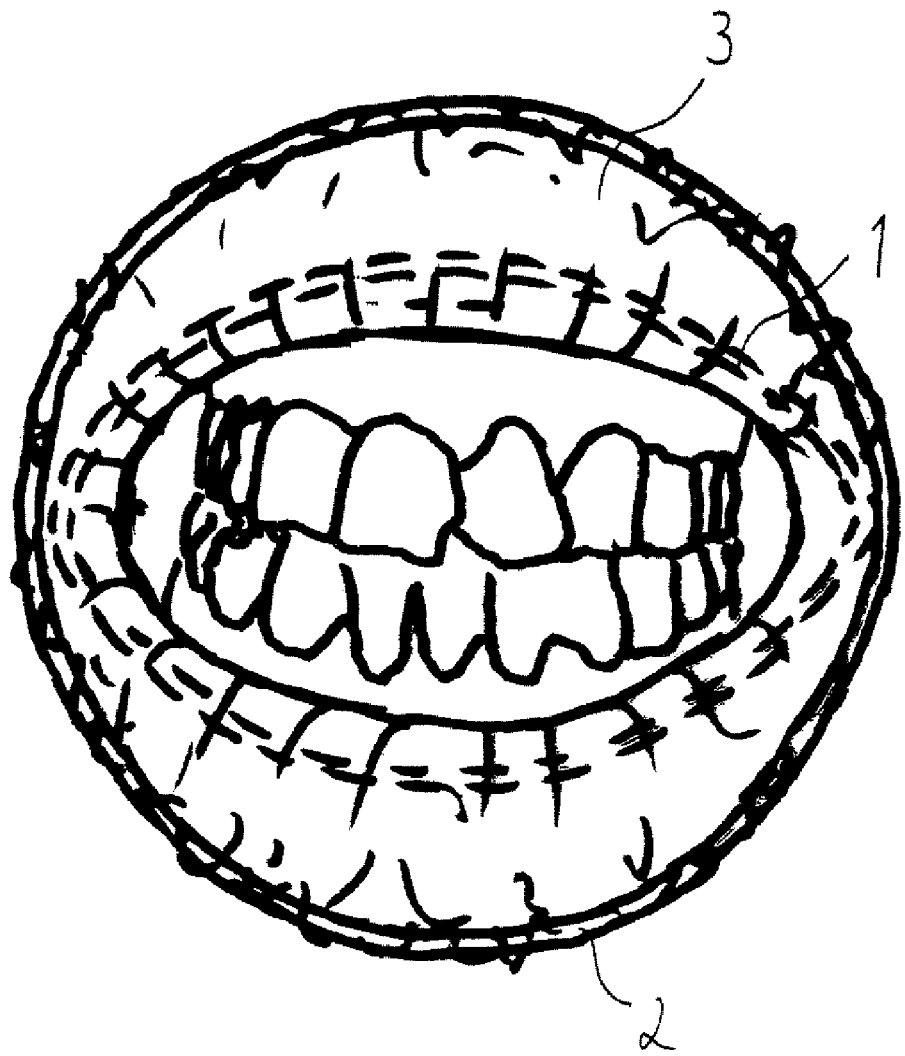

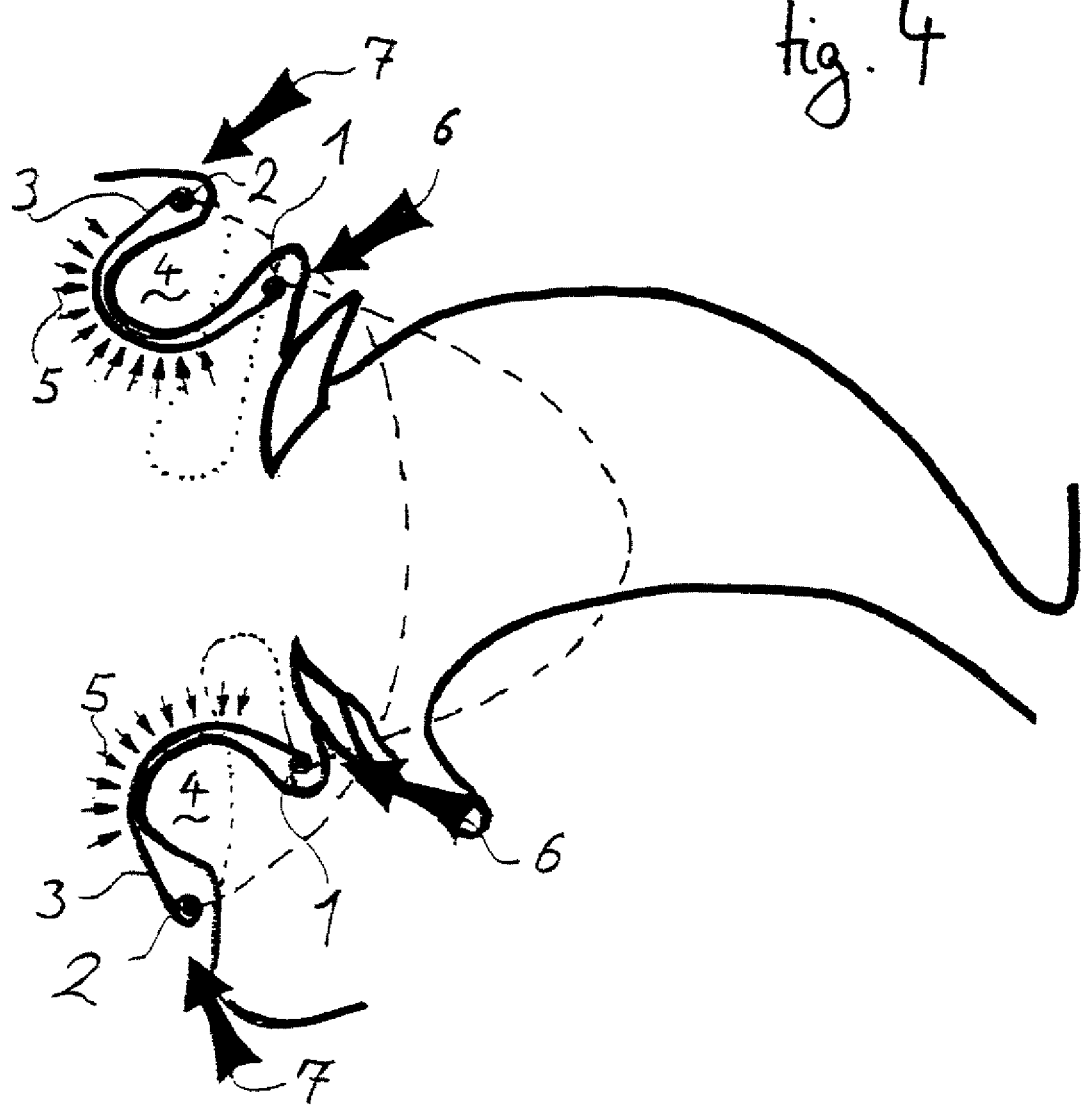

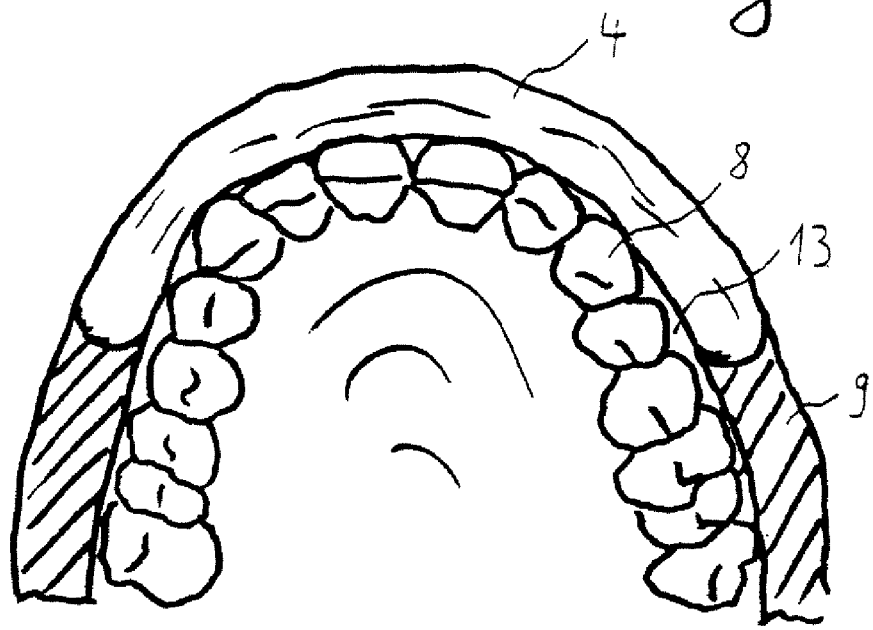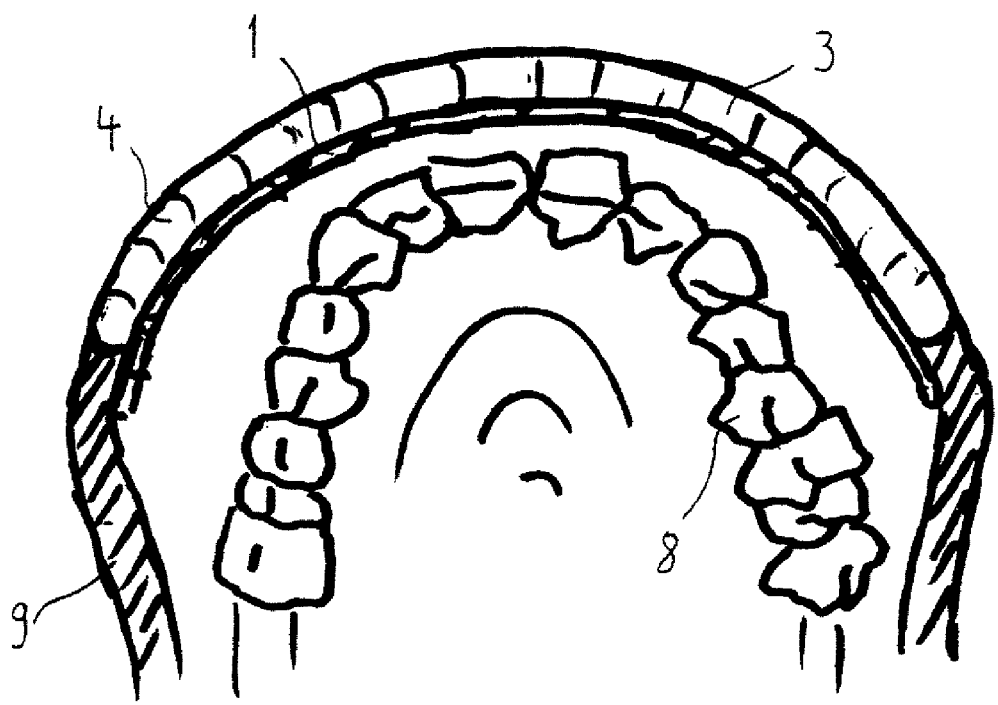

LIP AND CHEEK EXPANDER

CROSS REFERENCES TO RELATED APPLICATIONS

This application is a continuation of U.S. application Ser. No. 10/468,934, filed Aug. 22, 2003, which is a national stage application under 35 U.S.C. §371 from PCT Application No. PCT/EP02/14342 filed Dec. 16, 2002, which claims the priority benefit of Switzerland application 2001 2305/01 filed Dec. 17, 2001.

BACKGROUND OF THE INVENTION

The invention relates to lip and cheek expanders for use when performing dental medicine, dental hygiene or dental-documenting activities.

During the aforementioned activities it is usually necessary to keep the lips and cheeks that come into abutment with the rows of teeth away from the rows of teeth, in order to free up a sufficient working space, to make the necessary inspection conditions possible and to reduce the risk of damage to the lips and cheeks.

When performing activities in the side area of a row of teeth, the respective cheek is kept away or retracted by exerting a force on the lip or the cheek via a so-called cheek retractor, via the mouth mirror or via a retractor hook. These pressure loadings can lead to pressure marks or swellings on the lips and cheeks or cause pain.

Such retractors, which are usually made of metal, are suitable exclusively for freeing up one side of a working space. To perform activities in different areas of the rows of teeth, however, cheek retractors designed in various ways are necessary for the retraction to be effective. Not least, mouth mirror, cheek retractor and retractor hook must be guided by hand. As a result, either the dentist providing the treatment now only has one hand at his disposal, and/or an assistant is needed in addition to hold the retractor. The restricted working space requires a precisely coordinated interplay of the movements of the person performing the treatment and the assistant. Moreover, with such instruments even the most skilled assistant cannot succeed in keeping away or retracting the sensitive lips, corners of the mouth and cheeks to the complete satisfaction of the patient and of the person performing the treatment.

Metal spreader clamps which expand the mouth opening are known for carrying out activities in the front area of the rows of teeth. These clamps can be provided with metal lip shields for the more uniform introduction of the spreading forces.

Spreader clamps are also known in which pre-formed lip shields and a spreading apparatus rigidly connected to the latter are formed by a single plastic injection-molded part. Unlike the previously mentioned metal instruments they do permit a somewhat gentler retraction on the one hand, but on the other hand a sterilization is possible only to a limited extent, as plastics that can be used for this purpose are generally not autoclavable. However, if sterilization is insufficient, herpes labialis for example, which frequently occurs on the lips and corners of the mouth, is easily transmissible.

Also, it is not possible with conventional instruments—because of their design—to keep the lips and cheeks away from the rows of teeth over their whole length at the same time. Moreover, patients find the alternate pushing and pulling with such instruments unpleasant.

Keeping away or retracting the lips and cheeks in question by means of conventional instruments on the one hand restricts access to the oral cavity and can on the other hand—in particular if fitted for a prolonged period—lead to traumatic postoperative phenomena in the area of the lips and cheeks.

Thus, a protective body with a pre-formed U-shaped longitudinal profile, which is made from a soft, elastic material, is known from DE 83 23 817 U1. If one of the lips is inserted into this U-shaped protective body, it is actively protected by the protective body against injuries caused by the treatment tools. This protection can be further increased by additionally incorporating into the U-shaped protective body reinforcements made of special steel wire. One embodiment of the invention ensures that the mouth opening is kept open, but not that the lips are kept away from the rows of teeth. For such a retraction in the front area, a further embodiment is disclosed which is characterized by a metal spacer bracket additionally attached to the protective body. This spacer bracket, which can be supported against the row of teeth lying behind the protected lip, ensures the desired distance between the lip and the row of teeth. However, painful pressure marks are usually caused by this type of support.

SUMMARY OF THE INVENTION

The object of the invention is therefore to remedy defects of the state of the art. In particular, a lip and cheek expander is to be proposed which is versatile in use and may be produced at low cost, and also simultaneously keeps away and protects the lips and cheeks coming to rest against the rows of teeth.

This object is achieved by a lip and cheek expander in which the characterizing features of the invention are implemented.

Further advantageous or alternative embodiments or developments of the invention are described in the features of the dependent patent claims.

When reference is made in connection with the invention to tensioning frames, these are to be understood in the broadest sense as spatial structures which can absorb pull forces of a pre-determined order of magnitude directed against the centre of the structure. Such tensioning frames can be constructed to be rigid or elastic, optionally plastically deformable in addition. Elastically constructed tensioning frames facilitate among other things the application of an expander according to the invention. They can be made for example from wire, from solid profiles, small tubes or other suitable hollow profiles, or consist of metal alloys, of plastics, of rubber or of composite materials. A tensioning frame can also consist of several parts which are joined together. At least one of these frame parts can be attachable to a saliva suction device and can be constructed as a small tube provided with holes.

Out of static considerations, the tensioning frames are usually constructed as closed tensioning frames. However, open tensioning frames are also possible and can be of advantage for special purposes. Open tensioning frames must be constructed to be more solid than closed tensioning frames in order to be able to withstand the loadings that occur when the expander is fitted.

If the tensioning frames, in particular in the two areas of the corners of the mouth, are constructed larger than the oral cavity, an expander according to the invention can effectively be prevented from slipping out or in. It is also conceivable to construct tensioning frames, in particular tensioning frames resting externally against the mouth opening, in an adjustable manner.

When reference is made in connection with the invention to film-like means, these are to be understood in the broadest sense as sheet objects which essentially offer no resistance to bending as compared to stretching. The film-like means can be made from elastically stretchable, but in principle also from non-stretchable, material.

Contrary to the state of the art, by lip and cheek expanders according to the invention a pressure force is exerted, distributed over a large area, via the film-like means on the lips and cheeks which are to be held back from the rows of teeth. The film-like means are connected at one end to an inner tensioning frame located inside the oral cavity and at the other end to an outer tensioning frame resting externally against the lips and cheeks.

The film-like means are advantageously constructed to be thin and elastic. In cooperation with elastic, optionally prebent tensioning frames adapted to the anatomical conditions, very simple, extremely flexible and widely usable lip and cheek expanders can be provided which offer many advantages compared with conventional retractors and spreader clamps.

Upon fitting of the expander, pressure forces are built up by the film-like means distributed over a large area and circularly around the mouth opening. Due to the low wall thickness and the elasticity of the film-like means, these forces are uniformly distributed and gently built up. Through a pre-determined material deficit of the film-like means, the pressure forces which gently keep the lips open can be controlled. In addition, the elastic tensioning frames exert pressure forces on the cheeks moderately and over large areas. As a result, the mouth opening can be circularly kept wide open and at the same time the lips and cheeks can be gently held back from the rows of teeth in a manner that is comfortable for the patient.

Through an application of for example lubricants, flavours, medicaments, ointments or emulsions to at least part areas of the film-like means, the patient's wearing comfort can be further increased or other advantageous effects can be achieved by the application of the expander according to the invention.

Due to the flexible design concept of the expander, the tissue dynamic is also essentially maintained when the expander is fitted. Thus, in the case of operations an additional retraction with a retractor hook or the mouth mirror is possible at any time.

Lips and the corners of the mouth are largely protected via the film-like means against injuries caused by the instruments used. They are also an effective protection against for example herpes labialis or easily tearing and bleeding rhagades. Troublesome facial hair is covered in areal circular manner around the oral cavity by the film-like means and thus interferes with neither inspection nor treatment.

As the expander—because of its flexible design—conforms to the lips and cheeks, following the given anatomy of the patient, the working space is not reduced and adversely affected by the expander.

Not least, the simple design of an expander according to the invention permits inexpensive production, which makes disposable use possible. The hygiene advantages associated with this are obvious.

BRIEF DESCRIPTION OF THE SEVERAL VIEWS OF THE DRAWINGS

The invention is explained in a purely exemplary manner in more detail below with reference to the figures of the drawings. Identical parts in different embodiments which perform the same functions are given the same designations and reference numbers below. There are shown in.

DETAILED DESCRIPTION OF THE INVENTION

Figure 1:
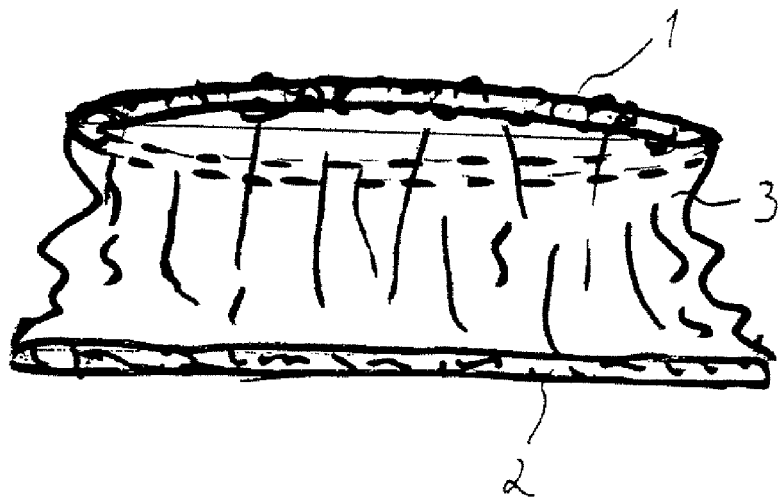
FIG. 1 a side view of a lip and cheek expander according to the invention when not fitted, FIG. 2 the lip and cheek expander according to the invention of FIG. 1 when not fitted, in plan view, FIG. 3 a lip and cheek expander according to the invention fitted to a mouth opening, in front view, FIG. 4 a partial view of the lip and cheek expander fitted to the mouth opening from FIG. 3, in section, FIG. 5 a partly sectioned view of the lower jaw prior to the insertion of a lip and cheek expander according to the invention, FIG. 6 a partly sectioned view of the lower jaw after the insertion of a lip and cheek expander according to the invention, FIG. 7 an enlarged view of the vicinity VII of the tensioning frames of the lip and cheek expander of FIG. 2, and FIG. 8 the film-like means prior to connection to the two tensioning frames.
Figure 2:
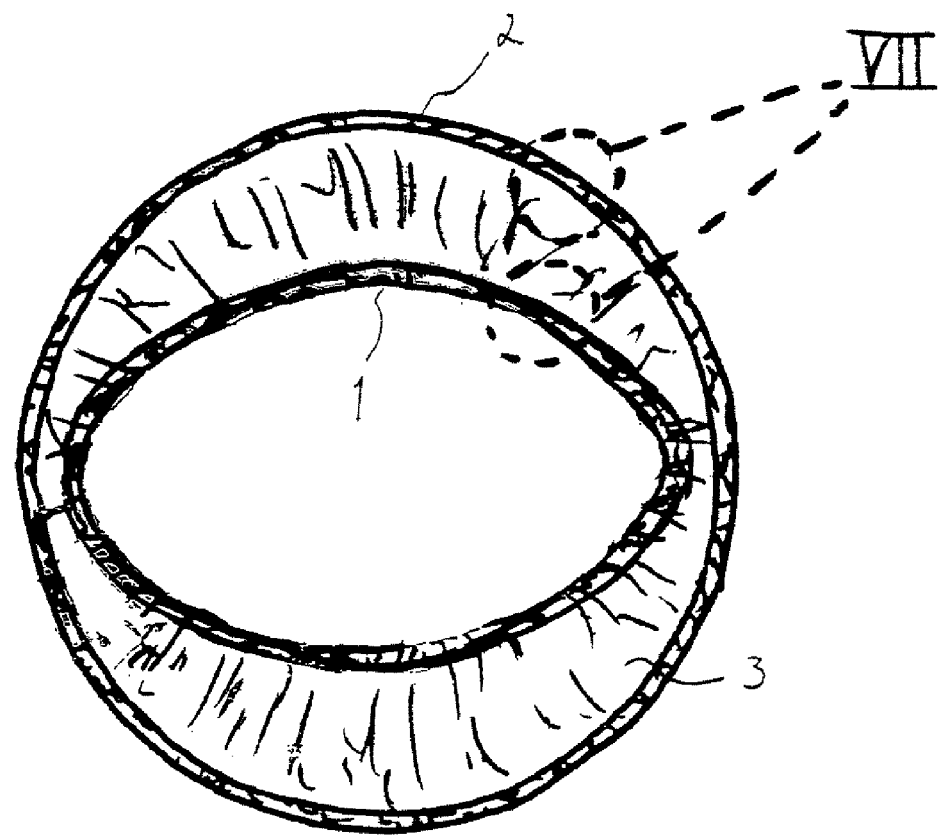

FIGS. 1 and 2 show an embodiment of a lip and cheek expander according to the invention when not fitted. This expander comprises two tensioning frames 1 and 2 which are constructed annularly closed, and film-like means 3 connecting the two tensioning frames 1 and 2. The means are constructed closed in the form of a circumferentially extending thin membrane.

In this embodiment, the tensioning frames 1 and 2 have the shape of differently sized, arched ellipses. They are constructed elastically bendable and can be made for example from a circumferentially extending special steel wire.

One of the tensioning frames, which according to FIG. 3 is arranged inside the oral cavity, the inner tensioning frame 1, has greater dimensions than the outer tensioning frame 2.

The inner tensioning frame 1 is connected to the outer tensioning frame 2 via the film-like means 3. The tensioning membrane, in a non-fitted state corresponding to FIG. 1, lacks a pre-determined shape and is tension-free. It is designed in the form of a thin, easily stretchable film and consists for example of elastic latex.

In this embodiment the inner tensioning frame 1 and the outer tensioning frame 2 are fixedly connected via an adhesive to the tensioning membrane over their full surface. However, it would also be possible to connect the film-like means 3 to the inner and the outer tensioning frame in a detachable manner via retaining folds or retaining hooks. The two tensioning frames 1 and 2 can also be wound round several times by the film. In this way the relatively small bearing surface of the metal tensioning frames 1 and 2 is greatly increased and made softer by means of the additional film material. The expander can thereby be made even more comfortable to wear.

FIG. 3 shows in front view the mouth opening of a person to whom the expander from FIGS. 1 and 2 is fitted. The inner tensioning frame 1 is indicated in FIG. 4 by broken lines.

Here, the tensioning membrane rests against the lips and the adjacent cheek areas and uniformly exerts a pressure force in an areally distributed manner. Due to the elastic design of the film-like means 3 as well as to a certain elastic flexibility of the inner tensioning frame 1 and the outer tensioning frame 2, respectively, the pressure force can be distributed essentially uniformly in combination with a coordinated dimensioning of these three components. In this way a uniform expansion of the lips and cheeks can also be achieved.

If the inner tensioning frame 1 has greater dimensions than the outer tensioning frame 2, the parts of the cheeks lying between the tensioning frames are tilted somewhat forward in the area of the small azimuths of the ellipses. In this way the cheeks are additionally kept even further away from the rows of teeth. The respective distance between the cheek and the rows of teeth can also be increased by a suitable shape of the inner tensioning frame 1, for example by additional, shield-like bulges in the area of the small azimuths of the ellipse.

Due to the dimensioning of the membrane, in this embodiment, in the area of the large azimuths of the ellipses, the inner tensioning frame 1 is located closer to the mouth opening than the outer tensioning frame 2. As a result, the inner tensioning frame 1 comes into contact with neither the lip frenulums nor the cheek frenulums. However, this could also be achieved by suitably pre-bent indentations of the inner tensioning frame.

The present invention makes possible on the one hand good access through the mouth opening and on the other hand the avoidance of painful pressure marks, even when an expander according to the invention is fitted for several hours. By means of an elastic construction of the components of the expander, optionally in combination with a manual plastic deformation of the tensioning frames, individually different anatomical conditions can normally be well compensated for. However, account can also be taken of these different conditions or special requirements as regards the distance between individual parts of the lips and cheeks and the rows of teeth, such as may be necessary in some treatments, by the use of suitably designed tensioning frames and membranes. Different types of expanders could be identified by different colours.

Due to the flexible construction and the elastic design of an expander according to the invention a closing of the dentition—even in the fitted state—is also possible. Also, when required, a specific area of the lips or cheeks can additionally be kept even further away from a row of teeth with a conventional rigid instrument.

FIG. 4 shows a section through the expander and the mouth opening of FIG. 3. Contrary to FIG. 3, the inner tensioning frame 1 and the outer tensioning frame 2 are visible. In the area of the mouth opening the film-like means 3 lie snugly against the lips 4. Uniform pressure forces 5 are exerted, areally distributed, on the lips 4 via the tensioning membrane. They counteract the closure and contraction forces of the lip and cheek muscles and bulge-likely compress the lips 4—starting from the normal position of the lips, indicated by dots. Circumferential pulling forces 6 and 7 corresponding to the pressure forces 5 are exerted by the tensioning membrane on the inner tensioning frame 1 and the outer tensioning frame 2, respectively. With a suitable construction of the tensioning frames 1 and 2, the pulling forces 6 and 7 can be absorbed virtually completely by these in the area shown. In this way, in this area the inner tensioning frame 1 exerts no contact forces on the respective mucous membrane of the lips. In other areas, on the other hand, only parts of the pulling forces 6 and 7 are absorbed by the tensioning frames 1 and 2, respectively. The resulting contact forces effect a corresponding abutment of the tensioning frames 1 and 2. The expander is kept stable by the equilibrium of the forces establishing around the mouth opening.

Thus, in order to insert the lip and cheek expander into the oral cavity of a patient in accordance with the intended purpose, the second tensioning frame 1 together with a part of the film-like means 3 is introduced into the patient's mouth and the first tensioning frame 2 placed around the mouth against the perioral areas of the face. In the process, the second tensioning frame 1 is elastically compressed in such a way that it can be inserted into the vestibule 13. After the release, the second tensioning frame 1, due to its elasticity, presses itself into the vestibule 13, as a result of which it pulls the film-like means 3 in the upper jaw and in the lower jaw along the vestibule 13 into the latter and retains it therein. In the process, the film-like means 3 is stretched. It can be seen from FIGS. 3 and 4 as well as from FIG. 6, which shows a view of the lower jaw after the insertion of the lip and cheek expander into the mouth, that the film-like means 3 extends from the tensioning frame 2 resting against the face along the skin of the face around the corners of the mouth and the lips 4 and intraorally in the vestibule 13. In this way lips and corners of the mouth are covered, so that the film-like means 3 represents a covering means. As described further above, the tensioning ring 2 clamped into the vestibule 13, together with the covering means 3, pushes apart upper and lower jaws vertically and corners of the mouth transversally. FIG. 5 shows a view of the lower jaw prior to the insertion of the lip and cheek expander into the oral cavity of a patient. The comparison between FIGS. 5 and 6 illustrates the retraction, effected by the lip and cheek expander, of the lips 4, the corners of the mouth and the cheeks 9 from the row of teeth 8 and the expansion thereby achieved of the vestibule 13, which creates an enlarged working space for the dentist.

Besides the closed design illustrated in the figures, the tensioning frames 1, 2 can, as already described, also be constructed to be open. In this case they are preferably connectable in such a way that, in this manner, they can be brought into an annularly closed form. Furthermore, the tensioning frames can have a large variety of different shapes. Thus it may be that the tensioning frames 1, 2 have an essentially elliptical basic shape or can be brought into an essentially elliptical basic shape. The tensioning frames 1, 2 can however also have a circular shape or be able to be brought into a circular shape, the second tensioning frame 1 having a smaller outer diameter than the first tensioning frame 2. In this case the outer diameter of the tensioning frames 1, 2 in the circular shape is advantageously 40 mm to 120 mm, and preferably about 75 mm for the second tensioning frame 1 and preferably about 95 mm for the first tensioning frame 2.

Figure 7:
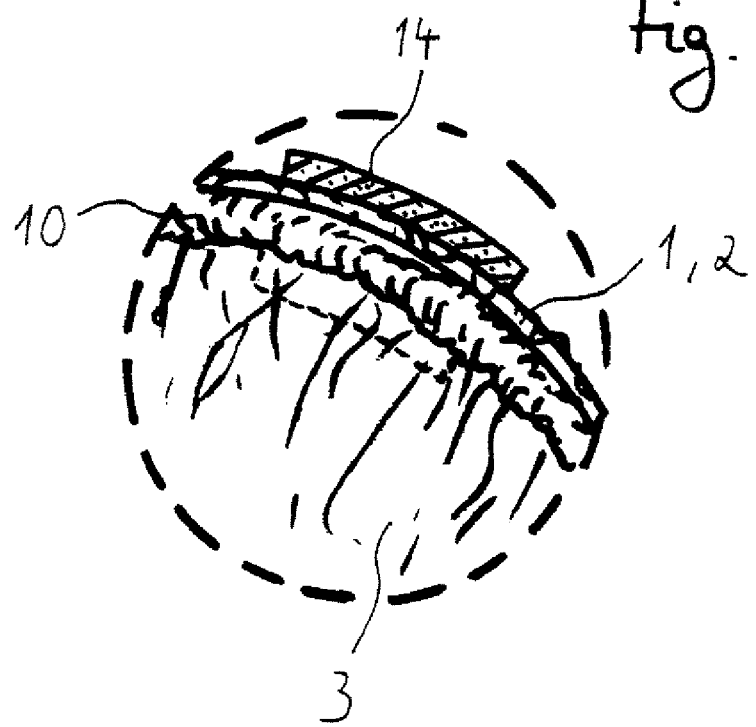

FIG. 7 shows in an enlarged representation a section of one of the two tensioning frames 1, 2 and of the adjacent covering means 3 connected to the latter. The two end portions of the covering means 3, along which the tensioning frames 1, 2 are disposed, are each rolled up in a direction extending essentially perpendicular to the tensioning frames 1, 2 to form a bulge 10. In this case, it is advantageous if the end portions 10, formed in the manner of a bulge, of the covering means 3 are constructed not to be unrollable, e.g. by using an adhesive or by sealing. In the embodiment of FIG. 7 the bulge-like end portions 10 of the covering means are each arranged at the inside of a tensioning frame 1, 2, wherein the bulge 10 may be adhesively connected to the tensioning frame 1, 2. The part of the covering means 3 extending from the bulge 10 is then preferably passed at least once around the tensioning frame 1, 2, so that the covering means 3 completely surrounds the tensioning frame 1, 2. However, it is also possible to form the bulge 10 around the tensioning frame 1, 2 so that the tensioning frame 1, 2 extends inside the bulge 10.

In this way, the covering means 3 can serve as a pressure pad with which at least the second tensioning frame 1 or else also both tensioning frames 1, 2 are advantageously provided and which extends along the tensioning frames 1, 2. However, it is also possible to provide alone or additionally a separate pressure pad 14 such as is shown in FIG. 7 and with which at least the second tensioning frame 1 is provided and which extends along the respective tensioning frame 1, 2. In this case, it is possible that this pressure pad 14 extends along the entire tensioning frame 1, 2 in question or else along one or more sections of the respective tensioning frame 1, 2. The pressure pad 14 preferably surrounds the respective tensioning frame 1, 2 and the bulge-like end portion 10, connected to the latter, of the covering means 3 and consists of a soft material which is advantageously foam.

Figure 8:
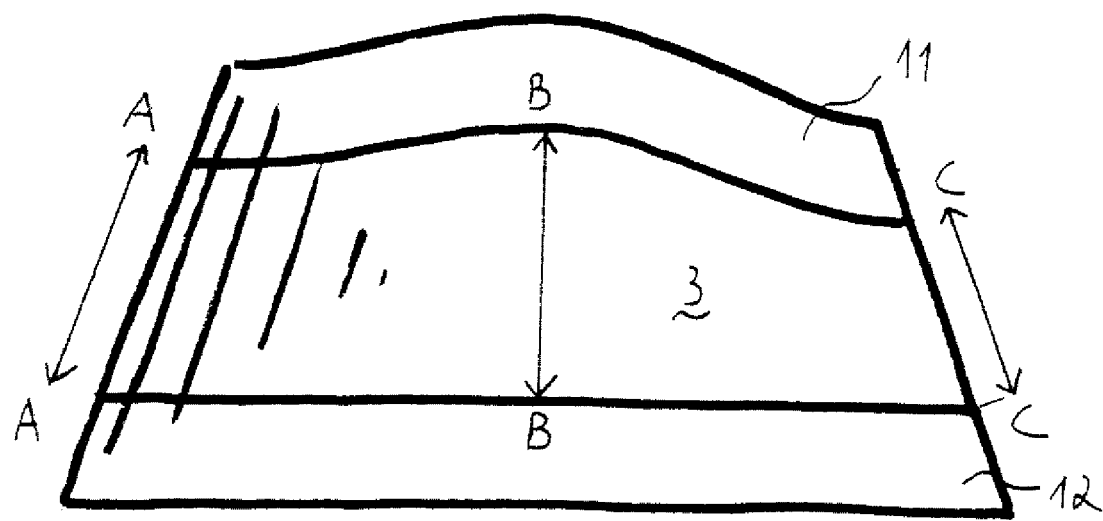

FIG. 8 shows the covering means 3 prior to the connection to the two tensioning frames 1, 2. The covering means 3 can have strip-shaped open or else a ring-shaped and thus tubularly closed design. It has two end portions 11, 12 along which the covering means 3 is connected to the tensioning frames 1, 2, which preferably is effected by winding these sections 11, 12 around the tensioning frames 1, 2. The dimensions of the covering means are preferably chosen such that they are about 30 mm along the line A-A which identifies the portion to be arranged in the area of the lower incisors, about 35 mm along the line B-B which identifies portions to be arranged in the area of the corners of the mouth, and about 25 mm along the line C-C which identifies the portion to be arranged in the area of the upper incisors. In each case the covering means 3 can be produced in standard sizes, for example for children and for adults.

The invention claimed is:

1. Device for covering the lips and corners of the mouth and for keeping away the lips, cheeks and corners of the mouth from the rows of teeth in the mouth of a patient comprising a first ellipsoidal shaped or circular shaped tensioning frame for external abutment against the mouth opening, a second, elastic ellipsoidal shaped or circular shaped tensioning frame for insertion into the vestibule of the patient's mouth and covering means having two opposing end portions connecting the tensioning frames, wherein the first tensioning frame is disposed along one end portion of the covering means and the second tensioning frame is disposed along the other end portion of the covering means, so that the inserted device is open towards the oral cavity, wherein the covering means is film-like and, when not inserted into the mouth, without a pre-determined shape, wherein in a condition of the device in which the covering means is not rolled around each of the tensioning frames more than once, the maximum distance from the first tensioning frame to the second tensioning frame is less than the maximum diameter of the first tensioning frame or of the second tensioning frame, and the second tensioning frame is adapted in order to be introduced into the patient's vestibule in an elastically deformed state and to intraorally fix the covering means, so that, when the device is inserted, the covering means extends between the extraoral first tensioning frame and the intraoral second tensioning frame in abutment to and around the lips and the corners of the mouth and exerts on them forces distributed over a large area, and that a pressure force is exerted on the lips, cheeks and corners of the mouth which pushes these away from the teeth and circularly biases the mouth opening into an open position, wherein the device permits the closing of the mouth.

2. Device according to claim 1, wherein the covering means and the tensioning frames are adapted in such a way that, when the device is inserted, an equilibrium of forces establishes between the covering means and the tensioning frames, in which equilibrium the pulling forces exerted by the covering means on the tensioning frames are absorbed by the latter in such a way that the second tensioning frame exerts no or only light contact forces on the respective mucous membranes in the area of the lips and the transfer of force from the device to lips, corners of the mouth and cheeks takes place essentially via the covering means.

3. Device according to claim 1, wherein the covering means is made from an elastically stretchable material.

4. Device according to claim 3, wherein the elastically stretchable material is latex.

5. Device according to claim 1, wherein the covering means has a tubularly closed design.

6. Device according to claim 1, wherein the first tensioning frame is rigid or elastic.

7. Device according to claim 1, wherein the tensioning frames are formed of wire, steel wire, spring steel wire, solid profiles or small tubes.

8. Device according to claim 1, wherein the tensioning frames are formed of metal alloys, plastics, rubber or composite materials.

9. Device according to claim 1, wherein the tensioning frames have an annularly closed design.

10. Device according to claim 1, wherein the tensioning frames have an essentially elliptical basic shape or can be brought into an essentially elliptical basic shape.

11. Device according to claim 1, wherein the first and the second tensioning frames have different dimensions.

12. Device according to claim 11, wherein the second tensioning frame has greater dimensions than the first tensioning frame.

13. Device according to claim 1, wherein the tensioning frames have a circular shape or can be brought into a circular shape, the second tensioning frame having a smaller outer diameter than the first tensioning frame.

14. Device according to claim 13, wherein the outer diameter of the second tensioning frame in the circular shape is 40 mm to 120 mm.

15. Device according to claim 13, wherein the outer diameter of the first tensioning frame in the circular shape is 40 mm to 120 mm.

16. Device according to claim 1, wherein at least one of the first tensioning frame and the second tensioning frame is fixedly connected to the covering means over the whole surface thereof.

17. Device according to claim 1, wherein the two end portions of the covering means, along which the tensioning frames are disposed, are each rolled up in a direction extending perpendicular to the tensioning frames to form a bulge.

18. Device according to claim 17, wherein the two end portions of the covering means, along which the tensioning frames are disposed, extend around the tensioning frames.

19. Device according to claim 17 wherein the end portions, formed into a bulge, of the covering means are constructed not to be unrollable.

20. Device according to claim 17, wherein the bulge-like end portions of the covering means are each arranged on the inside of a tensioning frame.

21. Device according to claim 1, wherein at least the second tensioning frame is provided with at least one pressure pad extending along the tensioning frame.

22. Device according to claim 21, wherein the pressure pad surrounds the second tensioning frame and the bulge-like end portion, connected thereto, of the covering means.

23. Device according to claim 21, wherein the pressure pad consists of a soft material.

24. Device according to claim 21, wherein the pressure pad is formed of foam.

25. Device according to claim 1, wherein the dimensions of the covering means in the direction of the connection line between the two tensioning frames is about 25 mm in the area of the upper incisors, about 30 mm in the area of the lower incisors and about 35 mm in the area of the corners of the mouth.

26. Device according to claim 1, wherein the second tensioning frame is adapted in such a way that, following the insertion into the mouth of a patient, it abuts intraorally buccally in the upper and lower gingivobuccal fold as well as on both sides, has a curve essentially corresponding to the dental arch and is spaced from buccal tooth surfaces of the upper jaw as well as of the lower jaw.

* * * * *